US008633690B2

(12) United States Patent
Feiweier et al.

(10) Patent No.: US 8,633,690 B2
(45) Date of Patent: Jan. 21, 2014

(54) METHOD OF OPERATING AN MRI IMAGING SYSTEM, WHILE ALSO CONTROLLING GRAADIENT AND SHIM SUB-SYSTEMS ALONG WITH THE MRI IMAGING SYSTEM

(75) Inventors: Thorsten Feiweier, Poxdorf (DE);
Daniel Fischer, Erlangen (DE);
Hendrik Jeschke, Spardorf (DE);
Thorsten Speckner, Nuremberg (DE);
Stephan Stoecker, Baiersdorf (DE)

(73) Assignee: Siemens Aktiengesellschaft, Munich (DE)

( * ) Notice: Subject to any disclaimer, the term of this patent is extended or adjusted under 35 U.S.C. 154(b) by 717 days.

(21) Appl. No.: 12/777,378

(22) Filed: May 11, 2010

(65) Prior Publication Data
US 2010/0286802 A1 Nov. 11, 2010

(30) Foreign Application Priority Data
May 11, 2009 (DE) .......................... 10 2009 020 661

(51) Int. Cl.
*G01R 33/54* (2006.01)
*G01R 33/546* (2006.01)
*A61B 5/055* (2006.01)

(52) U.S. Cl.
USPC ............ 324/307; 324/309; 324/318; 600/410

(58) Field of Classification Search
USPC .......................... 324/300–322; 382/128–131; 600/407–435; 700/90
See application file for complete search history.

(56) References Cited

U.S. PATENT DOCUMENTS

| 2,777,011 | A  | * | 1/1957  | Marks          | 348/42  |
|-----------|----|---|---------|----------------|---------|
| 3,491,286 | A  | * | 1/1970  | Simpson        | 324/304 |
| 6,023,634 | A  | * | 2/2000  | Hanawa et al.  | 600/410 |
| 6,477,398 | B1 | * | 11/2002 | Mills          | 600/409 |
| 6,509,735 | B2 |   | 1/2003  | Mueller et al. | 324/307 |
| 6,801,037 | B1 | * | 10/2004 | Zhang          | 324/309 |
| 6,850,793 | B1 | * | 2/2005  | Miyazaki et al.| 600/410 |
| 7,081,750 | B1 | * | 7/2006  | Zhang          | 324/309 |
| 7,183,770 | B2 | * | 2/2007  | Grasslin et al.| 324/322 |
| 7,218,113 | B2 | * | 5/2007  | Feiweier et al.| 324/320 |
| 7,245,125 | B2 | * | 7/2007  | Harer et al.   | 324/310 |
| 7,372,270 | B2 |   | 5/2008  | Sung et al.    | 324/314 |
| 7,657,071 | B2 | * | 2/2010  | Bartesaghi et al.| 600/410 |
| 7,659,720 | B2 | * | 2/2010  | Furudate et al.| 324/318 |
| 7,785,098 | B1 | * | 8/2010  | Appleby et al. | 425/470 |
| 7,821,267 | B2 | * | 10/2010 | Yatsui et al.  | 324/318 |
| 7,864,999 | B2 | * | 1/2011  | Chang et al.   | 382/128 |
| 7,881,878 | B2 | * | 2/2011  | Burrus et al.  | 702/28  |

(Continued)

*Primary Examiner* — Melissa Koval
*Assistant Examiner* — Tiffany Fetzner
(74) *Attorney, Agent, or Firm* — Schiff Hardin LLP

(57) ABSTRACT

In an imaging system having a number of subsystems and a control device that controls the subsystems in a coordinated manner to implement a measurement sequence and an operating method therefor, sequence control data that define different functional sub-sequences of the measurement sequence are transmitted to the control device. Different active volumes are associated with the functional sub-sequences. In addition to the sequence control data, active volume position data are provided to the control device that define bearing and extent of the active volumes associated with the different functional sub-sequences. Control signals to implement the measurement sequence for the different subsystems are generated automatically by the control device based on the sequence control data and the active volume position data so that the individual functional sub-sequences are locally optimized at least with regard to a sub-region of their associated active volume.

9 Claims, 6 Drawing Sheets

(56) References Cited

U.S. PATENT DOCUMENTS

| | | | |
|---|---|---|---|
| 7,893,413 B1* | 2/2011 | Appleby et al. | 250/505.1 |
| 8,049,193 B1* | 11/2011 | Appleby et al. | 250/505.1 |
| 2003/0191386 A1 | 10/2003 | Heid | 600/410 |
| 2005/0073303 A1* | 4/2005 | Harer et al. | 324/309 |
| 2005/0073304 A1 | 4/2005 | Feiweier et al. | 324/307 |
| 2005/0154291 A1* | 7/2005 | Zhao et al. | 600/410 |
| 2005/0189940 A1 | 9/2005 | Feiweier et al. | 324/307 |
| 2006/0054810 A1* | 3/2006 | Grasslin et al. | 250/299 |
| 2006/0229856 A1* | 10/2006 | Burrus et al. | 703/11 |
| 2006/0281987 A1* | 12/2006 | Bartesaghi et al. | 600/410 |
| 2007/0110290 A1* | 5/2007 | Chang et al. | 382/128 |
| 2007/0265813 A1* | 11/2007 | Unal et al. | 703/2 |
| 2008/0071167 A1* | 3/2008 | Ikedo et al. | 600/419 |
| 2008/0180104 A1* | 7/2008 | Furudate | 324/318 |
| 2009/0309595 A1* | 12/2009 | Yatsui | 324/309 |
| 2010/0286802 A1* | 11/2010 | Feiweier et al. | 700/90 |

* cited by examiner

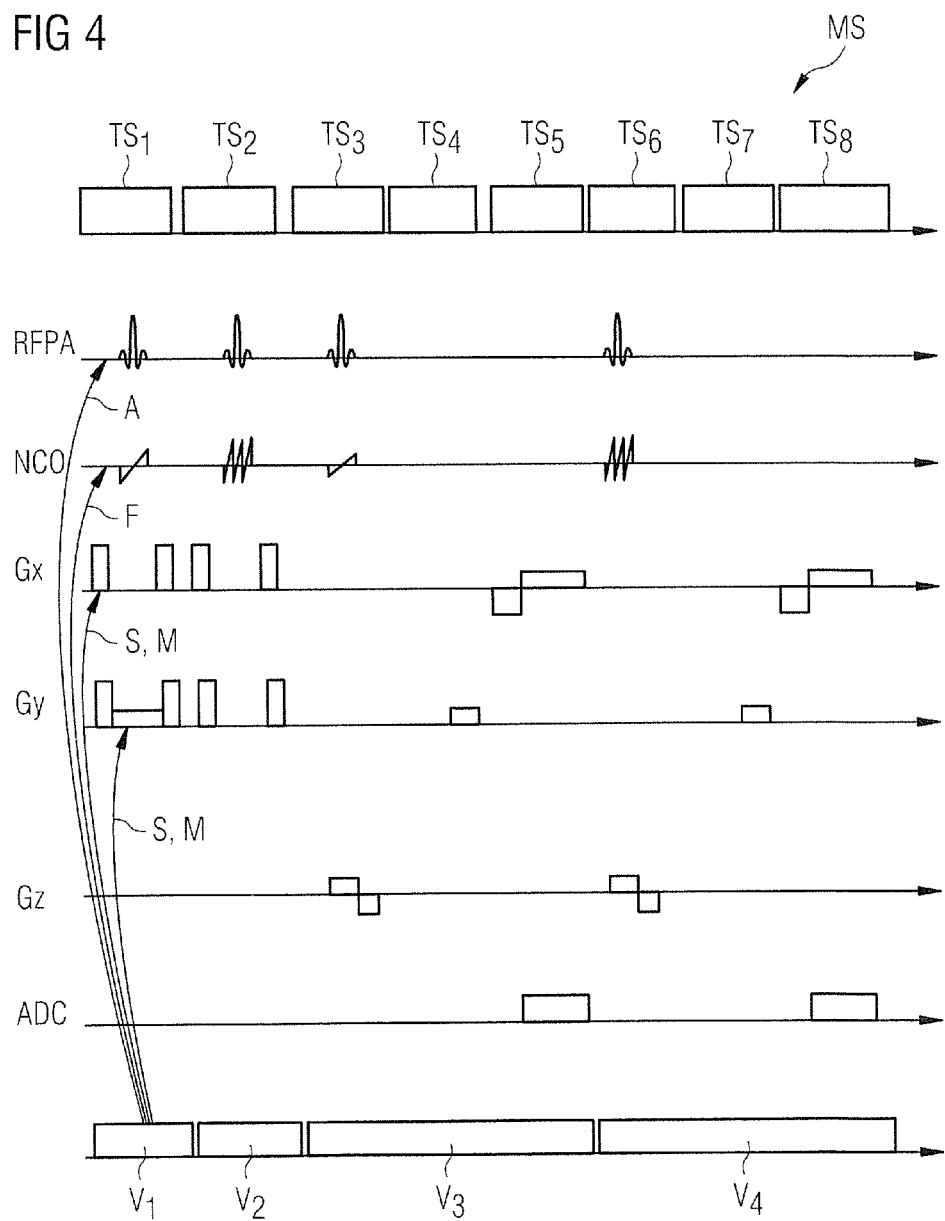

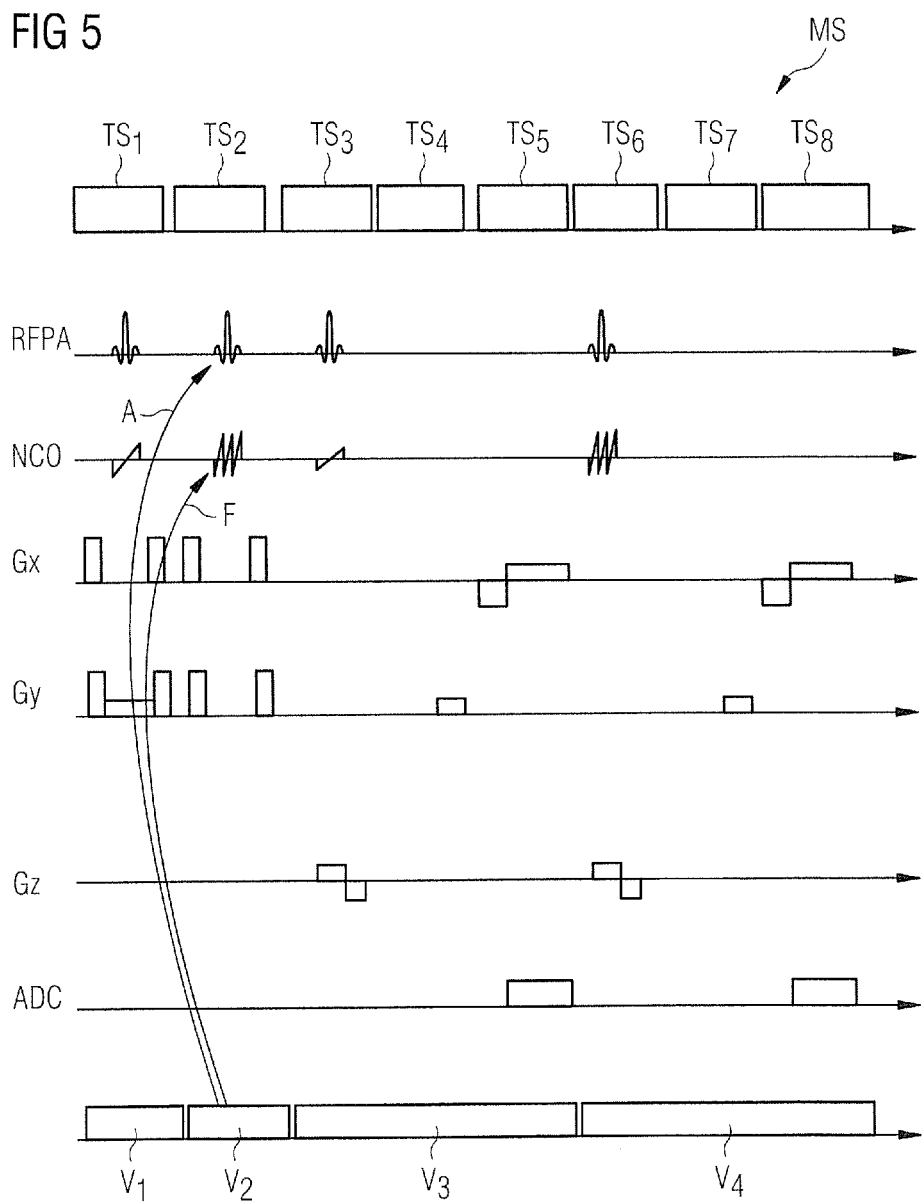

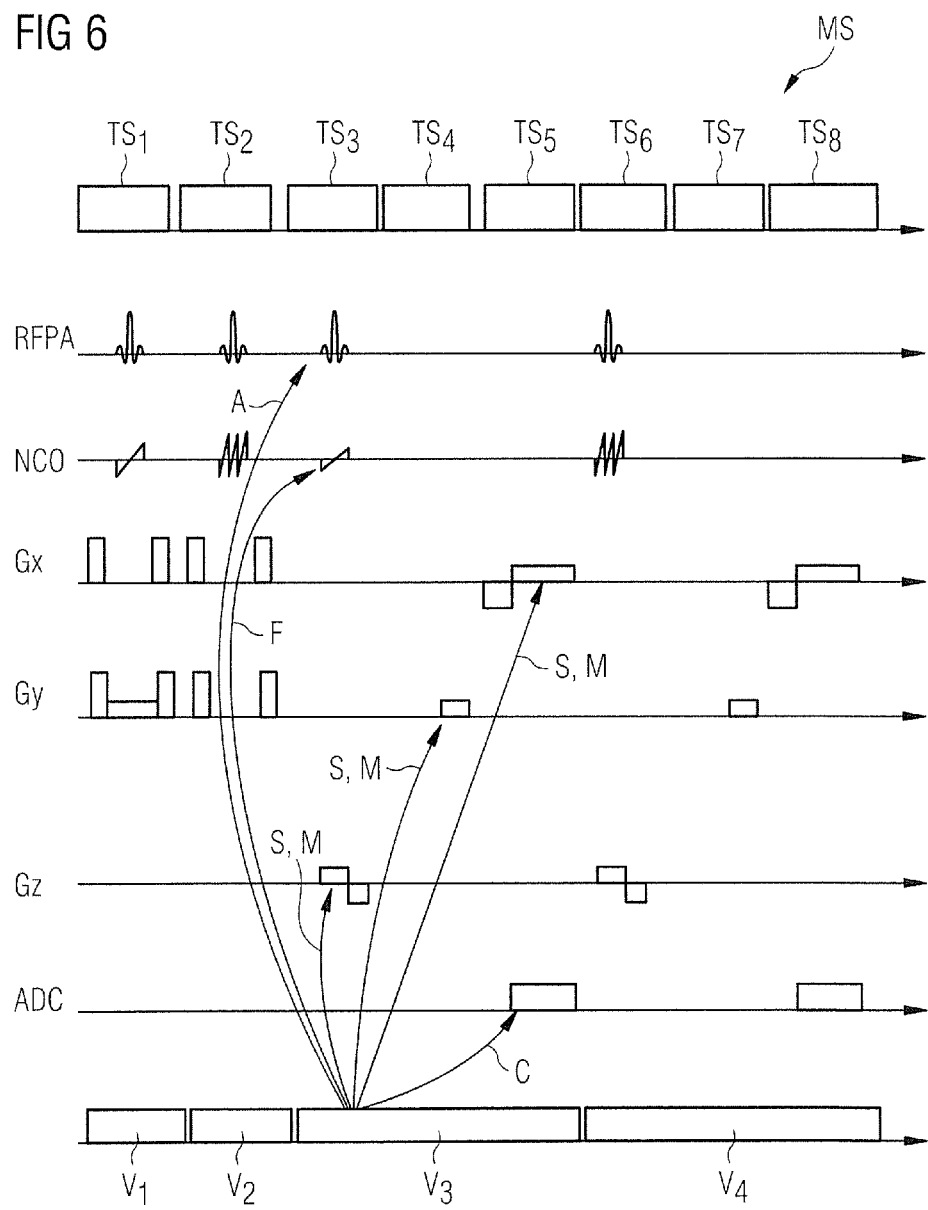

METHOD OF OPERATING AN MRI IMAGING SYSTEM, WHILE ALSO CONTROLLING GRAADIENT AND SHIM SUB-SYSTEMS ALONG WITH THE MRI IMAGING SYSTEM

BACKGROUND OF THE INVENTION

1. Field of the Invention

The present invention concerns a method to operate an imaging system, in particular a magnetic resonance system, with a number of subsystems and a control device that controls the subsystems in a coordinated manner to implement a measurement sequence. For this sequence control data which define different functional sub-sequences of the measurement sequence are provided to the control device, wherein different active volumes are associated with the functional sub-sequences. Moreover, the invention concerns an imaging system with a number of subsystems and a control device to implement this method.

2. Description of the Prior Art

Tomographical imaging systems (for example magnetic resonance apparatuses or computed tomography systems) are complex installations with multiple technical subsystems. Among these (for example in a magnetic resonance system) are the basic field magnet system in order to expose a body to be examined to a relatively high basic magnetic field, for example 1.5 Tesla or even 3 Tesla in newer systems, known as high magnetic field systems; a gradient system in order to additionally apply a magnetic field gradient; and a shim system in order to homogenize the magnetic fields. Moreover, such a magnetic resonance system has a radio-frequency transmission system in order to emit a radio-frequency excitation signal with suitable antenna devices. This excitation signal causes the nuclear spins of specific atoms excited to resonance by this radio-frequency field to be tilted by a specific flip angle relative to the magnetic field lines of the basic magnetic field. An additional subsystem required by the magnetic resonance system is a radio-frequency reception system which serves to receive and additionally process the radio-frequency signal radiated upon relaxation of the nuclear spins (known as the magnetic resonance signal) so that the desired image data can be reconstructed from the raw data acquired in this manner. For spatial coding, defined magnetic field gradients respectively generated by means of a gradient system are superimposed on the basic magnetic field during the transmission and readout or (reception) of the radio-frequency signals.

All of these technical modules must be operated in a coordinated fashion and in a suitable manner by a controller. The adjustments and switchings of the individual subsystems that are necessary for a specific imaging process must be activated at the respective correct points in time. Within an imaging workflow, the volume to be imaged is typically acquired in sub-volumes, for example in multiple slices in 2D imaging or in what are known as multiple "slabs" in 3D imaging. The sub-volumes that are acquired in this way are then assembled into a complete volume. An additional definition of sub-volumes can result via "regions of interest" that can be specifically defined by the operator, for example. Furthermore, additional sub-volumes result given the establishment of local saturation regions or local preparation or labeling pulses, for example in magnetic resonance systems.

As mentioned above, sequence control data (most often within a measurement protocol) are transmitted to the control device for coordinated control. These sequence control data define different functional sub-sequences of a complete measurement sequence. For example, in a magnetic resonance acquisition a first sub-sequence can be a pulse sequence in order to locally achieve a saturation in a specific region. Additional sub-sequences can contain specific preparation pulses, for example, and other sub-sequences serve again for the successive excitation and to receive the magnetic resonance signals in different slices or slabs. It is normally the case that different active volumes are associated with the different functional sub-sequences, meaning that a different sub-volume of the entire measurement volume is relevant for each sub-sequence. In general, however, no information or at best limited information about the occupation in space (i.e. the position and orientation) and the extent of the different sub-volumes is provided to the technical subsystems. Therefore, information about the spatial occupation and extent of the sub-volumes have previously been used only in the spatial selection (i.e. given a specific slice and slab excitation or a very specific regional saturation) in the control of the individual subsystems in tomographical imaging methods. For example, in magnetic resonance apparatuses a slice-selection gradient is applied in a targeted manner simultaneously with a radio-frequency excitation pulse of suitable shape and frequency in order to excite a specific slice. Moreover, it has previously been the case that only proprietary optimization methods have been known in which it is sought to optimize the image quality via specific activation of individual subsystems depending on defined sub-volumes.

In DE 10 2004 002 009 A1 a method is described for local homogenization of the radio-frequency field distribution of RF pulses in a determinable active volume. In U.S. Pat. No. 7,372,270 a method is likewise described for compensation of inhomogeneities of the RF excitation field. A method to measure the RF field distribution for a possible optimization is described in DE 103 38 075 A1 In U.S. Pat. No. 6,509,735 a method is explained for updating the global imaging parameter given a movement of an examination subject. DE 102 14 736 A1 is concerned with the optimization of k-space trajectories, i.e. with the optimal adjustments of the gradients for spatial coding in a magnetic resonance apparatus. However, all of these methods deal only with the setting of individual subsystems of the magnetic resonance system.

However, in most systems the actual optimization of the different sub-sequences to the associated active volumes ensues only by virtue of the developer of a control protocol modifying the sequence control data in a suitable manner, meaning that he or she must calculate, in a suitably tailored sequence, control data on the basis of his or her knowledge of the desired sub-volumes, or the active volumes belonging to the sub-sequences, and then correspondingly change the control protocol so that a suitable control locally optimized to the active volume ensues in this way for the individual sub-sequences.

This method is extraordinarily time-consuming, and places markedly high demands on the developers of the control sequences. A "normal" operator of a magnetic resonance apparatus is then generally no longer in the position to vary a control protocol (if necessary) and adapt it to an examination without having to be concerned that the optimization of the individual sub-sequences with regard to the associated active volumes will be lost. Furthermore, the developer of the control sequence in this case must have detailed knowledge about the subsystems in order to be able to make the corresponding modifications at all. A poorer optimization in turn leads to worse measurement results, which in the extreme case can lead to the situation that the generated images are not useful and a greater risk of misinterpretations exists, or measurements must be repeated, which causes additional stress for the patient.

SUMMARY OF THE INVENTION

An object of the present invention is to further develop a method to control an imaging system as well as an imaging system such that the quality of the imaging method and of the image data generated therewith is increased without additional effort, or with as little additional effort as possible.

In the method according to the invention, in addition to the sequence control data (also called sequence control parameters) active volume position data are provided that define the spatial occupation and extent of the active volumes associated with the different functional sub-sequences. Control signals to implement the measurement sequence for the different subsystems are then generated automatically by the control device based on the sequence control data and the active volume position data so that the individual functional sub-sequences are locally optimized in a wholly automatic manner, at least with regard to a sub-region of their associated active volume.

It is thus no longer necessary to calculate the sequence control data with knowledge of the individual active volumes and to corresponding pass it to the control device (which is different than has been the case in the past); rather, it is sufficient to pass the sequence control data in a form that is not optimized to the volume. The active volume position data can instead be passed separately to the control device, for example via a suitable interface, via query by the operator within an inactive dialog or via separate specification within a control protocol. The active volume position data must exactly establish only the bearing and the extent of at least the partial region of the active volumes of the different functional sub-sequences that is provided for the optimization and establish the association with the individual sub-sequences. The optimization, i.e. the determination of the matching control signals for the different subsystems in order to implement the complete measurement sequence with all sub-sequences in a locally optimized manner, then ensues without intervention of the operator within the control device, with necessary adjustments and dynamic parameter settings of all technical subsystems being oriented toward the active volume or the respective sub-region of the active volume.

With this method it is thus ensured that all sub-sequences can always ensue optimized locally to the respective significant volume without complicated prior calculations by the operator being required for this purpose. An optimal image quality thus can be ensured in a particularly simple manner. For example, if an operator would like to modify a control protocol in order to use a somewhat different sub-sequence within a measurement sequence or in order to associate a different active volume with a specific sub-sequence, the operator can input the commands separate from one another or modify them in the control protocol, which is significantly simpler, safer and faster than if the operator must initially modify the sequence control data for the sub-sequence himself or herself so that these are optimized with regard to a different active volume.

An imaging system according to the invention requires a control device fashioned according to the invention. This control device must be able to automatically generate the control signals to implement the measurement sequence for the different subsystems based on sequence control data and based on separately received active volume position data so that the individual functional sub-sequences are locally optimized at least with regard to a sub-region of their associated active volume. The components that are required for this in the control device can advantageously be realized in the form of software modules on a processor or multiple processors of the control device that are networked among one another. Such a realization in software has the advantage that conventional imaging systems can also be retrofitted quickly and cost-effectively in the manner according to the invention. The invention therefore also encompasses a computer-readable storage medium that can be loaded directly into a memory of a programmable control device of an imaging system, and is encoded with program code segments in order to execute all steps of the method according to the invention that is described above when the program is executed in the control device.

In principle the method according to the invention is usable in various imaging systems, in particular tomographical imaging systems such as magnetic resonance tomography systems, computed tomography systems, PET apparatuses, SPECT apparatuses, systems operating with ultrasound etc. The method offers particular advantages in magnetic resonance apparatuses which normally possess the subsystems described above, namely a basic magnetic field system, a gradient coil system, a shim system, a radio-frequency transmission system and a radio-frequency reception system.

For example, in magnetic resonance tomographs different technical subsystems can be optimized automatically as follows.

In radio-frequency transmission systems, the homogeneity of the transmission field within the current active volume can be optimized dynamically via what is known as a $B_1$ shimming or via matching selection of the two-dimensional or three-dimensional excitation pulses. The average amplitude of the transmission field can likewise be optimized dynamically in what is known as a transmission adjustment.

With regard to the radio-frequency reception system, a dynamic selection of the acquisition coils for the current active volume can optimally ensue with regard to the signal-to-noise ratio (SNR) and/or according to iPAT criteria (a method to accelerate the image acquisition).

Furthermore, in NCOs (Numerical Controlled Oscillators) which determine the basic frequency of the system the dynamic setting of the basic frequency can be optimized for the current active volume within the scope of a frequency adjustment.

In shim systems a dynamic setting of the shim currents of the first, second and if necessary even higher order is possible such that the basic magnetic field in the current active volume is homogenized (what is known as "$B_0$ shimming").

Moreover, a Maxwell field compensation is possible in which the action of Maxwell fields is dynamically minimized via switching of compensation fields of first, second and if necessary higher order, as well as via adaptation of the basic frequency in the active volume. Such a Maxwell correction is often required because normally no field rising spatially linearly, exclusively in the direction of the z-axis, can be generated upon activation of a gradient; rather, according to the Maxwell equations transversal components are always created that are also active in terms of magnetic resonance. The real resonance frequency then does not correspond to the desired resonance frequency. However, these deviations can be calculated analytically. Corrections based on which the Maxwell field terms can be corrected can accordingly be calculated insofar as the position (i.e. the active volume to be optimized) is known.

In principle, such a local optimization can ensue via a control device with different control components, meaning that a control component for optimization of the radio-frequency transmission amplitude and pulse shape, a control component to optimize the NCO and a control component to optimize the radio-frequency acquisition system etc. are used, for example. However, the optimization of the functional sub-sequences preferably ensues by means of a central optimization device of the control device to which the active volume position data are transmitted. Such a central optimization device is equivalent to multiple optimization modules that cooperate in a coordinated, suitable manner, for example by being centrally controlled in turn by a "master module" or the like. A centrally controlled optimization of the subsystems and sub-sequences has the advantage that cross-dependencies can be taken into account. For example, in a magnetic resonance measurement the active volume is defined by the slice to be acquired during the data acquisition in which a readout gradient must be active. For optimization of the image quality, possible interfering Maxwell fields must be taken into account; in particular the zeroth order must be suitably set by the adaptation of the basic frequency. At the same time the basic frequency must also be adjusted for this active volume. For this purpose, the control of the NCO responsible for the basic frequency must ensue in a suitably coordinated manner.

The local optimization of a functional sub-sequence advantageously ensues with regard to an optimization volume located within the associated active volume, i.e. again a sub-volume having a particular value in the optimization, and being limited within the active volume. In such a case it can also be sufficient for the active volume position data that are transmitted to the control device for local optimization to include only the bearing and extent of at least the sub-region of the appertaining active volumes. However, in principle it is also possible for the control unit, within the active volume, to establish an optimization volume at which the local optimization ensues, the optimization volume being based on other boundary conditions.

Such an optimization volume can advantageously be determined for a functional sub-sequence by calculating an intersection of the active volume (associated with the functional sub-sequence) with a subject volume, wherein this subject volume contains the subject information about a specific examination subject to be examined. For example, the active volume in which a specific sub-sequence should act can be a complete acquisition slice, and if the examination subject is the entire body of the patient this subject occupies only a central region of the active volume slice surrounded by air (which is displayed in the image as a noise region). Since an optimization of the technical subsystems is only meaningful for the region that delivers actual image information, an additional (advantageously fully automatic) limitation of the optimization volume in the explained manner is useful. The same applies if, for example, only one specific organ or one specific structure (for example the spinal column) whose volume can also already be defined is to be examined within the body of a patient or test subject. In this case the organ or the specific structure to be examined within the body is to be viewed as an examination subject, and an intersection of this subject volume with the active volume can likewise ensue in order to determine the optimization volume.

For example, an automation of this process can ensue by determining the subject volume on the basis of image data generated by the imaging system. Such image data are advantageously one or more overview images—known as "localizers"—of the body or body region containing the examination subject. Such an overview image can be processed in a suitable manner in order, for example, to segment regions with subject information of the desired subject and such without the desired subject information, and to determine the optimization volume by averaging from the subject volume that is automatically determined in this manner as well as the provided active volume (for example the slice to be excited).

In a further preferred variant of the method, at least a portion of the active volume position data is determined automatically from the sequence control data. For this purpose, the sequence control data (which do not need to be matched to the specific active volume) are analyzed as to whether they are directed toward a specific active volume, and corresponding active volume position data are then automatically generated. This is possible with the use of suitable heuristic algorithms. For example, the bearing, orientation and extent of the excited slice result from the frequency and bandwidth of an RF excitation pulse with knowledge of the simultaneously acting slice selection gradients. The active volume position data generated in this manner are then provided for the generation of the control signals for the implementation of the measurement sequence.

BRIEF DESCRIPTION OF THE DRAWINGS

FIG. 4 is a very simplified exemplary embodiment of a measurement sequence with multiple sub-sequences and their associated active volumes with a depiction of the parameters for the individual subsystems that are optimized for the first sub-sequence at the first active volume, FIG. 5 shows the measurement sequence with the individual sub-sequences and associated active volumes as in FIG. 4, but with a depiction of the parameters of the subsystems that are optimized for the second sub-sequence at the second active volume.

FIG. 6 shows the measurement sequence with the individual sub-sequences and associated active volumes as in FIG. 4, however with a depiction of the parameters of the subsystems that are optimized for the third active volume.

DESCRIPTION OF THE PREFERRED EMBODIMENTS

Figure 1:
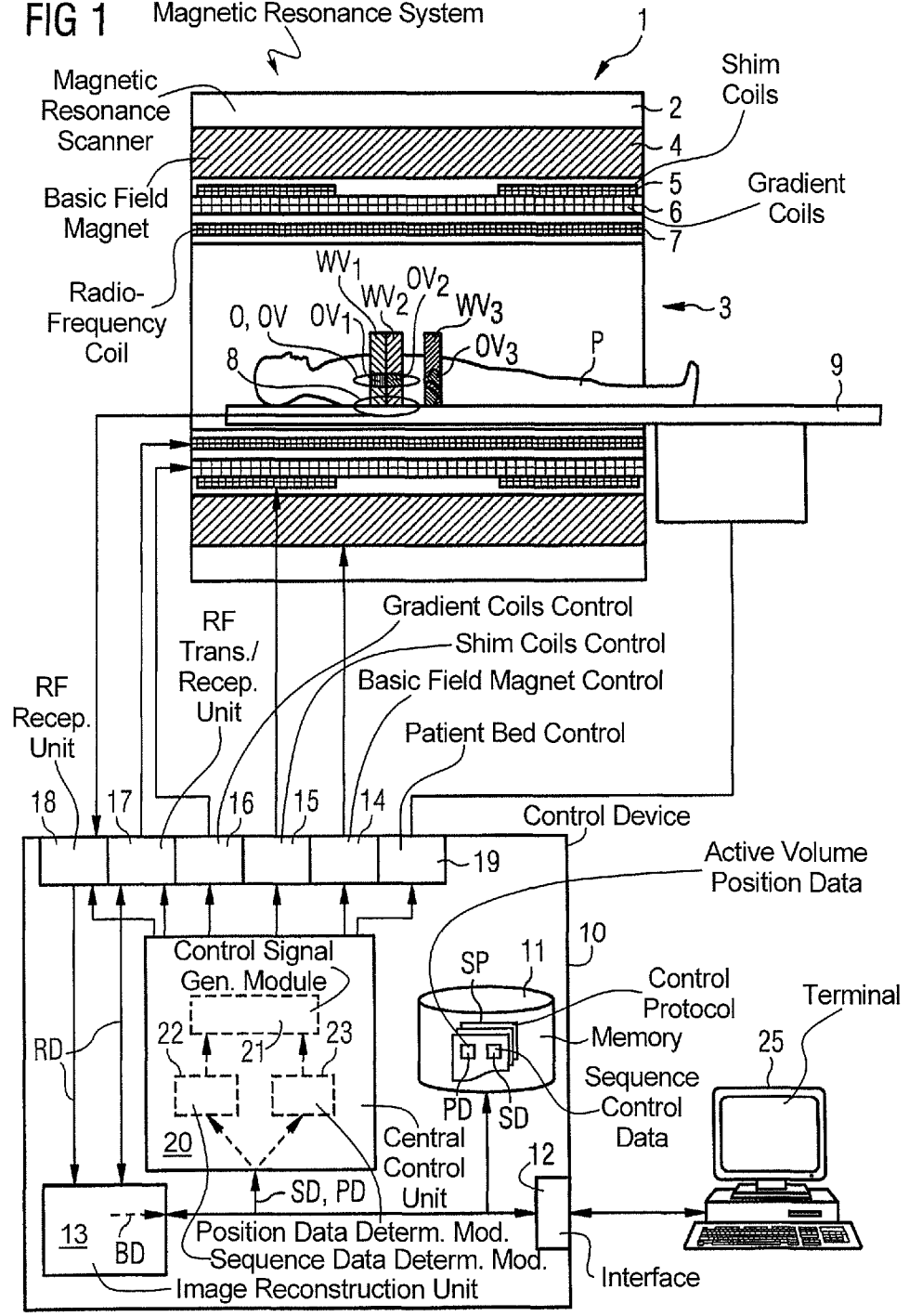
FIG. 1 schematically illustrates an exemplary embodiment of a magnetic resonance system according to the invention.

A magnetic resonance system 1 according to the invention is shown schematically in FIG. 1. It includes the actual magnetic resonance scanner 2 with an examination space 3 or patient tunnel located therein. A bed unit 9 can be driven into this patient tunnel 3 so that, during an examination, a patient P or test subject lying thereupon can be supported at a specific position within the magnetic resonance scanner 2 relative to the magnet system and radio-frequency system arranged in the magnetic resonance scanner 2, or can be moved between different positions during a measurement. At this point it is noted that the precise design of the magnetic resonance scanner 2 is not significant. For example, a cylindrical system with a typical patient tunnel can be used, as well as a C-arm-shaped magnetic resonance apparatus which is open to one side.

Basic components of the magnetic resonance scanner are a basic field magnet 4, a number of shim coils 5 and magnetic field gradient coils 6, as well as a whole body radio-frequency coil 7. The acquisition of magnetic resonance signals induced in the examination subject can ensue via the whole body coil 7 with which normally the radio-frequency signals are also emitted to induce the magnetic resonance signals. However, it is also possible to receive these signals with local coils placed on or below the patient, for example. All of these components are known in principle to those skilled in the art and are therefore only schematically depicted in FIG. 1.

The individual components are controlled by a control device 10 that here is depicted in the form of a common block. This can be a control computer which can be formed by a number of individual computers (possibly computers that are spatially separated and connected with one another via suitable cabling or the like). This control device 10 is connected via a terminal interface 12 with a terminal 25 with which an operator can control the entire system 1.

This control device 10 has, among other things, a basic magnetic field control arrangement 14, a shim coil control arrangement 15 and a gradient coil control arrangement 16. The whole body coil 7 is activated and read out via a radio-frequency (RF) transmission/reception unit 17. The radio-frequency transmission portion of the radio-frequency transmission/reception unit 17 includes, for example, a radio-frequency pulse amplifier to amplify and shape the radio-frequency pulses, and an NCO to establish the frequency. Local coils 8 (if present) are read out via an additional radio-frequency reception unit 18. This radio-frequency reception unit 18 can include, for example, a coil selection unit in order to respectively select the matching local coil from multiple available local coils. A patient bed control unit 19 serves to control the bed unit 9.

The basic field magnet 4, together with its control arrangement 14, forms the basic magnetic field system 4, 14; the shim coils 5 with the associated control arrangement 15 form the shim system 5, 15; the magnetic field gradient coils 6 with the associated control arrangement 16 form the gradient system 6, 16; the radio-frequency coil 7 together with its radio-frequency transmission/reception unit 17 forms a radio-frequency transmission/reception system 7, 17; and the local coils 8 together with their radio-frequency reception unit 18 form an additional radio-frequency reception system 8, 18.

All control arrangements 14, 15, 16, 19 and the radio-frequency transmission and/or reception units 17, 18 are controlled in a coordinated manner by a central control unit 20 so that the basic magnetic fields, gradient fields and radio-frequency pulses required for the implementation of a measurement are output synchronously, the shim coils are correctly set and the bed unit 7 is also situated at the correct position. Moreover, for this purpose, it must be ensured that the signals at the local coils 8 are read out by the radio-frequency reception unit 18 at the matching point in time, or signals at the whole body coil 7 are read out and correspondingly processed further by the radio-frequency transmission/reception unit 17.

The signals or raw data RD acquired in this way are then relayed to an image reconstruction unit 13 in which the desired magnetic resonance image data BD are reconstructed in order to then output an image (for example to the screen of the terminal 25) or store them in a memory 11.

Such a magnetic resonance scanner 2 and the associated control device 10 can include additional components that are not explained in detail herein. In particular, the system 1 can also be coupled via a suitable interface with a network—for example a radiological information system (RIS)—in order to receive control protocols that can be used at the system 1, or in order to send magnetic resonance image data (generated by the system 1, for example), to store said magnetic resonance image data in external mass storage or to pass them to finding stations or printers or the like.

The generation of the control signals for the individual control arrangements 14, 15, 16, 17 and the radio-frequency transmission and/or reception units 18, 19 by the central control unit 21 here ensues via a control signal generation module 20 realized in the form of software on a processor of the control device 10, which control signal generation module 21 generates the control signals ST on the basis of sequence control data SD that define different sub-sequences of the complete measurement sequence. An example of such a measurement sequence composed of multiple sub-sequences is explained later using FIGS. 4 through 6. These sequence control data SD are typically established within control protocols SP that can be stored in a memory 11 of the system 1. Such a control protocol SP contains all control data that are necessary for a smooth workflow of a specific measurement sequence. For example, the operator can select (for example via a suitable user interface by means of the terminal 25) a control protocol SP for a measurement to be implemented and then can implement the measurement wholly automatically using this control protocol SP. However, it also possible for the operator to retrieve and modify a control protocol in order to implement special measurements, for example. It is also likewise possible to select control protocols SP via an additional network interface (not shown) on other computers, in particular control protocols provided by the manufacturer of the magnetic resonance system or by special service providers dealing with the development of control protocols.

Figure 2:
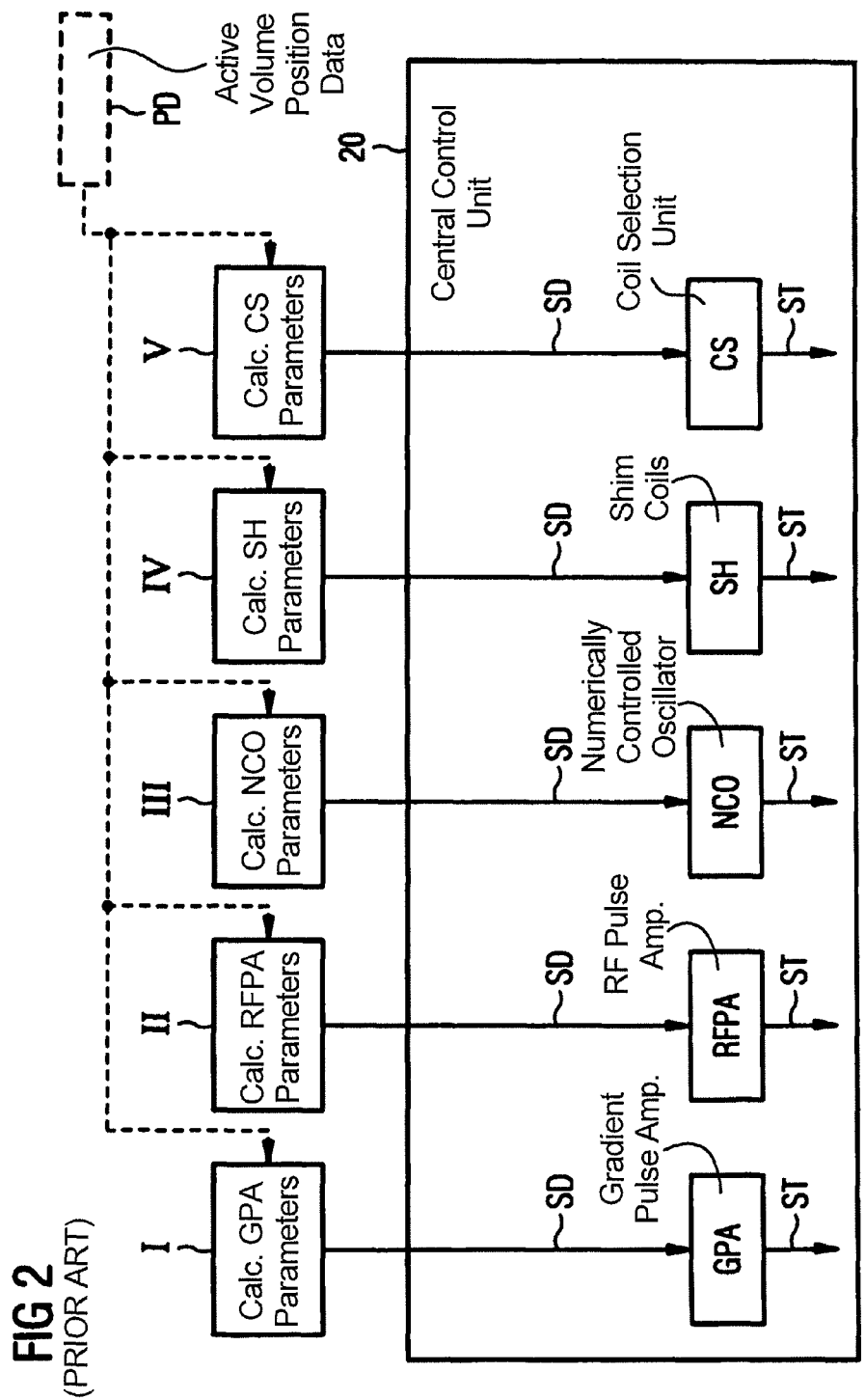
FIG. 2 schematically illustrates the procedure for control of subsystems of a magnetic resonance system according to the prior art.

As explained in detail above, to achieve an optimally good image quality it is helpful for the individual subsystems for a specific sub-sequence to be controlled so that they are optimized with respect to the active volume that is significant for the specific sub-sequence, or a specific portion of this sub-sequence. This has previously ensued by the developer of a control protocol already taking into account which active volume is relevant for which sub-sequence, and then correspondingly modifying the sequence control data or the parameters for the subsystems in the control protocol so that an optimization in the defined active volume is achieved with the sub-sequence. This is schematically depicted in FIG. 2. In the method steps I through V, the sequence control data (and thus the parameters for the different subsystems) are calculated under consideration of the spatial information (i.e. the active volume position data PD) that must be known to the protocol developer, and the sequence control data are passed to the central control unit 20 which—based on these parameters—determines and outputs the control signals ST for the individual subsystems. For example, in method step I the parameters for a gradient pulse amplifier GPA are calculated; the parameters for a radio-frequency pulse amplifier RFPA are calculated in method step II; the parameters for an oscillator NCO are calculated in method step III; the parameters for the shim coils SH are calculated in method step IV; and the parameters for a coil selection unit CS for selection of suitable coils are calculated in method step V. It is clear that these method steps I, II, III, IV and V can ensue in parallel or in an arbitrary order. As explained in the preceding, the sequence control parameters that are thereby established are normally stored in a control protocol and passed together to the central control unit 20 within the scope of this control protocol at an arbitrary later point in time.

Figure 3:
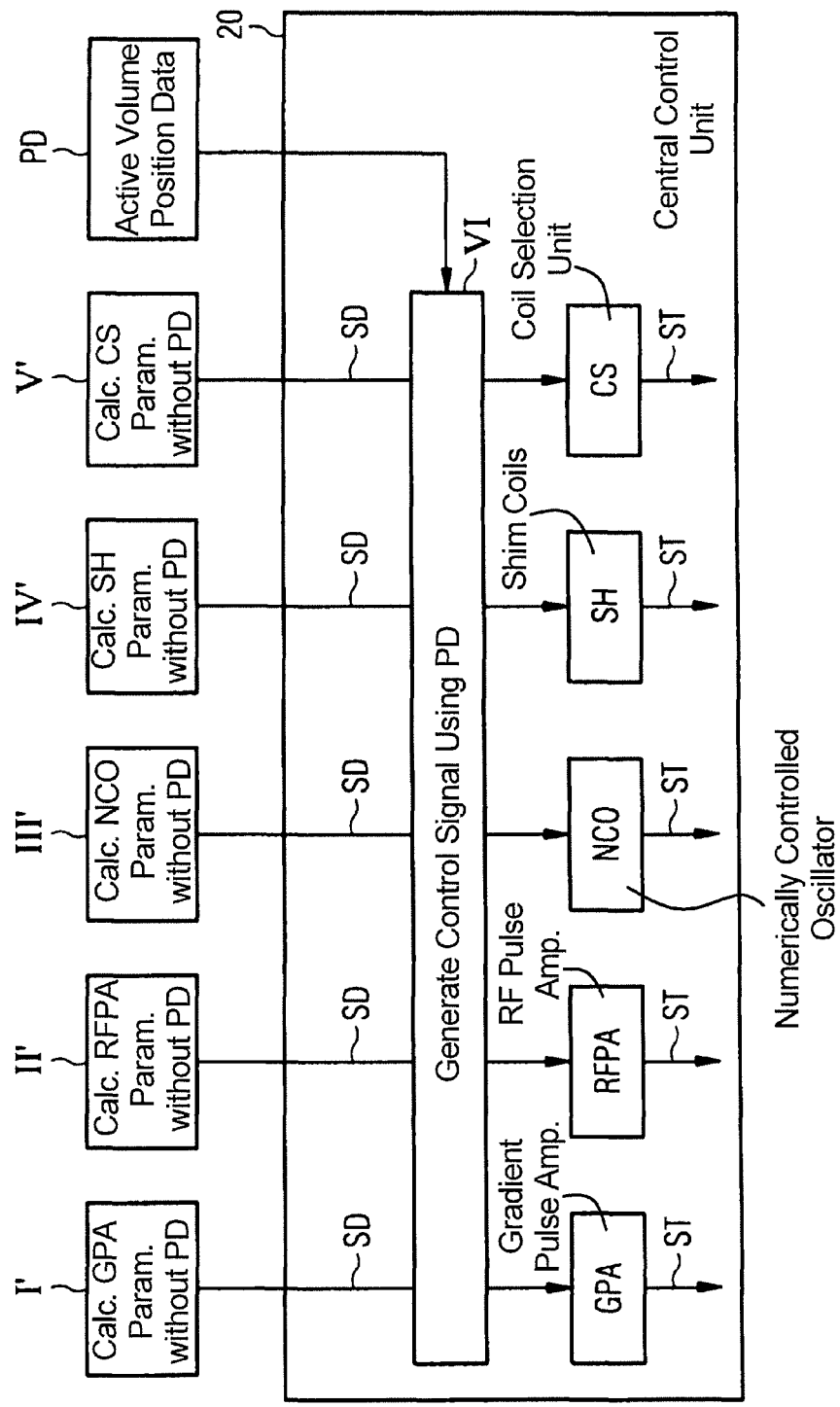
FIG. 3 schematically illustrates the procedure for a control of subsystems of a magnetic resonance system in the manner according to the invention.

In comparison to this, FIG. 3 shows the method according to the invention. In method steps I', II', III', IV', V' it is not required that the active volume position data PD are already taken into account and calculated in by the developer of the control protocol. Instead of this, in addition to the parameters or the sequence control data from method steps I', II', III', IV', V' that are not tailored to the active volume. Instead the active volume position data PD are passed or transmitted to the control device 20. For example, for this purpose the active volume position data PD can be written into the control protocol in one way, separately from the sequence control data SD for definition of the partial sequences, and if necessary be modified separately by an operator after retrieving such a control protocol in order to associate a different active volume with a specific sub-sequence. Active volume position data can alternatively be determined at least partially automatically from the sequence control data with the aid of suitable heuristic algorithms.

In a method step VI that is implemented wholly automatically in the central control unit 20, the control signals ST for the different subsystems are then respectively generated on the basis of the received sequence control data and the separately received active volume position data for the individual active volumes associated with the different sub-sequences, such that the sub-sequences are optimized with respect to the associated active volumes. The gradient pulse amplifier GPA, the radio-frequency pulse amplifier RFPA, the oscillator NCO, the shim coils SH and the coil selection unit CS are system components of the gradient system 6, 16, the basic magnetic field system 4, 14, the shim system 5, 15, the radio-frequency transmission/reception system 7, 17 and/or the radio-frequency reception system 8, 18, such that the control signals ST correspondingly affect the various subsystems 4, 5, 6, 7, 8, 14, 15, 16, 17, 18.

For this purpose, the central control unit 20 can include, for example, possess a sequence data determination module 22 in addition to a control signal generation module 21. The sequence control data determination module 22 detects and reads out the sequence control data SD within a control protocol SP. The central control unit 20 preferably additionally possesses a position data determination module 23 which detects the active volume position data PD in the control protocol SP, and the sequence control data and position data that are obtained in this way are then processed in a suitable manner by the control signal generation module 21 in order to achieve the desired optimization. In principle the sequence control data determination module 22 and the position data determination module 23 can also be realized as a combined module that detects the sequence control data SD and the active volume position data PD and passes them to the control signal generation module 21. Furthermore, the sequence control data determination module and the position data determination module can also be integrated into the control signal generation module 21. However, in FIG. 1 a separate depiction of these modules was selected in order to clarify that the optimization towards the active volumes associated with the individual sub-sequences of the measurement sequence only ensues fully automatically in the central control unit 20.

One example of when this is reasonable is likewise schematically depicted in FIG. 1 at the patient P in patient tunnel 3. Shown here are three different slices for which specific sub-sequences should be implemented within a measurement sequence. Each of these slices possesses a very specific active volume $WV_1$, $WV_2$, $WV_3$, wherein only a portion of this volume actually constitutes a part of the patient P to be examined. Regions in this active volume $WV_1$, $WV_2$, $WV_3$ outside of the patient body do not carry any significant image information at all. Therefore it is reasonable to use only the partial region of the active volume $WV_1$, $WV_2$, $WV_3$ which coincides with the body of the patient P. In the third slice $WV_3$ this optimization volume $OV_3$ is the entire region that results as an intersection between the active volume $WV_3$ and the volume of the patient body.

An additional variant is shown using the other two active volumes $WV_1$, $WV_2$. Here it is assumed that a specific organ O as an examination subject O should be examined within the body of the patient P. This organ O has a specific subject volume OV. Since only this volume OV is of interest, here the intersection of the subject volume OV with the active volumes $WV_1$, $WV_2$ is formed in order to find the respective optimization volumes $OV_1$, $OV_2$.

The possibilities of optimizing the individual subsystems towards an active volume associated with a specific sub-sequence are explained again using a concrete but very simplified measurement sequence MS with reference to FIGS. 4 through 6.

In the uppermost line, various sub-sequences $TS_1$, $TS_2$, ..., $TS_8$ are labeled. Shown in the lowermost column are the active volumes $V_1$, $V_2$, $V_3$, $V_4$ associated with these sub-sequences $TS_1$, $TS_2$, ..., $TS_8$ of the measurement sequence MS.

From this it is apparent that the first sub-sequence $TS_1$ is associated with a first active volume $V_1$ and the second sub-sequence $TS_2$ is associated with a first active volume $V_2$. A common active volume $V_3$ is associated with the sub-sequences $TS_3$, $TS_4$, $TS_6$. An active volume $V_4$ is likewise associated with the sub-sequences $TS_6$, $TS_7$, $TS_8$.

The pulses to be output by the subsystems are respectively shown separately on separate time rays for the individual sub-sequences between the lower line and the upper line. This means that the individual sub-sequences $TS_1$, $TS_2$, ..., $TS_8$ are implemented via the synchronous output of the respective pulses shown below the sub-sequences $TS_1$, $TS_2$, ..., $TS_8$ marked below the blocks or adjustment of the corresponding parameters at the subsystems. In the line second from the top, the radio-frequency pulse shapes and amplitudes that are to be output by the radio-frequency pulse amplifier RFPA are symbolically depicted. The respective NCO frequency to be adjusted is symbolized in the second line, wherein the slope of the curve symbolizes the frequency level. The gradient pulses Gx, Gy, Gz are drawn in the subsequent lines, and the readout window in which an analog/digital converter ADC for readout of a selected acquisition coil is activated is drawn in the penultimate line.

The first sub-sequence $TS_1$ of the measurement sequence MS here serves for a regional saturation, meaning that all nuclei within a regionally limited active volume $V_1$ are saturated. For this short, intensive Gx and Gy gradients are initially switched for dephasing. A radio-frequency pulse of a specific shape and amplitude is subsequently emitted with a specific frequency output by the NCO, while at the same time an additional Gy gradient pulse is emitted for slice selection. This sub-sequence terminates with an additional short, intensive gradient pulse in the x-direction and y-direction for dephasing.

With regard to the active volume $V_1$, different parameters can be optimized automatically by the control device (since this active volume $V_1$ is known). The amplitude A of the radio-frequency pulse to be emitted and the frequency F that is output by the NCO are optimized simultaneously. Moreover, the shim offset S for the gradient coils Gx, Gy can be suitably adjusted, for example, and equally suitable parameters for a Maxwell correction M can also be passed here. The parameters locally optimized depending on the respective active volume $V_1$ are depicted in FIG. 4 as arrows emanating from the lower line of the first volume $V_1$.

An additional sub-sequence $TS_2$ which immediately follows the first sub-sequence $TS_1$ is a chemical saturation, for example a fat saturation. This ensues very similar to the regional saturation via emission of a radio-frequency pulse with a specific amplitude and a frequency provided by the NCO, wherein here the frequency is higher than given the regional saturation in the sub-sequence $TS_1$. Here as well only the dephasing pulses in the Gx and Gy gradient are respectively switched before emission of the radio-frequency pulse and after the emission of the radio-frequency pulse. The emission of a Gy gradient for slice selection (as in the first sub-sequence $TS_1$) does not ensue since the saturation should ensue globally, meaning that the active volume $V_2$ here is the entire volume in the measurement space. In FIG. 5 it is shown how the amplitude A and the frequency F for the current active volume $V_2$ are optimized in this sub-sequence $TS_2$, for example.

After this chemical saturation $TS_2$, the actual acquisition of raw data for a first slice then ensues by means of three sub-sequences $TS_3$, $TS_4$, $TS_5$ which all must act on the appertaining slice. This slice defines the associated active volume $V_3$. The first sub-sequence $TS_3$ thereby serves for slice excitation in the active volume $V_3$. This ensues via emission of a radio-frequency pulse RF with a specific amplitude and a frequency provided by the NCO, with simultaneous emission of a Gz slice gradient pulse and a subsequent shorter, negative Gz rephasing pulse. The next sub-sequence $TS_4$ serves for spatial coding. For this only one Gy gradient pulse is switched. In the subsequent sub-sequence $TS_5$, the readout of the magnetic resonance signals generated in the active volume $V_3$ ensues in that initially a negative Gx gradient pulse for dephasing followed by a positive Gx gradient pulse for rephasing are emitted, wherein at the same time the ADC for readout is activated. The measurement of this slice is subsequently ended. Optimizable parameters are thereby shown again in FIG. 6 using arrows: the amplitude A of the emitted radio-frequency pulse; the frequency F of the NCO that is set upon output of the radio-frequency pulse; and—given the switching of the gradient pulses Gx, Gy, Gz—again the respective parameters for the shim offset S and the Maxwell correction parameters M. With regard to the ADC, an optimization can ensue to the effect that the best coil combination (symbolized by the coil selection parameter C) is selected for the appertaining active volume $V_3$ insofar as different readout coils (for example multiple local coils) are provided.

Finally, an excitation of an additional slice with which the data from the volume $V_3$ are read out can then ensue within the sub-sequence $TS_6$. This additional slice is represented here by the active volume $V_4$. A sub-sequence $TS_7$ for phase coding and an additional sub-sequence $TS_8$ to read out the slice then also ensue to determine the image data in the active volume $V_4$, in the same manner as in the first slice (i.e. in the active volume $V_3$).

It is clear that additional slices can be read out in the same manner, wherein corresponding sub-sequences must be repeated. Additional saturation sub-sequences or other special sub-sequences—for example for labeling or, respectively, marking of blood or other fluids whose course in the body should be established later—can likewise also be inserted in an arbitrary manner between the measurement of slices. The different possibilities to optimize parameters of the different subsystems for the individual sub-sequences with regard to the associated active volumes a correspond to the number of the possible sub-sequences and the associated active volumes.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method of operating a magnetic resonance imaging system comprising
    a plurality of subsystems including at least:
        a gradient coil sub-system and
        a shim sub-system; and
    a control device that operates the subsystems in coordination with each other in order to implement a data acquisition sequence and in order to acquire image data from an examination subject,
    said method comprising the steps of:
        supplying sequence control data to said control device that define a complete data acquisition sequence comprised of a plurality of respective different functional sub-sequences, each sub-sequence being associated with a respective active volume that is defined at a spatial location within the imaging system in which the respective functional sub-sequence is configured to be effective in said complete data acquisition sequence, the respective spatial locations of the active volumes for the respective different functional sub-sequences being different from each other;
        in addition to said sequence control data, receiving, with said control device active volume position data respectively associated with each of the different functional sub-sequences, and in said active volume position data defining, for each of said active volumes, a position, orientation and extent of the respective active volume in the imaging system; and
        in said control device, automatically generating respective control signals that operate each of the different subsystems in order to implement said complete data acquisition sequence, by using said sequence control data and said active volume position data, in order to locally optimize the respective different functional sub-sequences, at least with regard to a portion of the active volume associated with the respective functional sub-sequence, and making said control signals available from an output of said control device in a form that operates said subsystems in order to implement said measurement sequence.

2. A method as claimed in claim 1 comprising locally optimizing said different functional sub-sequences with respect to at least a portion of the respective active volumes within a central optimization module of said control device into which said active volume position data are supplied.

3. A method as claimed in claim 1 comprising locally optimizing said different functional sub-sequences with respect to a defined optimization volume situated within the respective active volume and associated with the respective functional sub-sequence.

4. A method as claimed in claim 3 comprising defining each optimization volume in said control device by calculating an intersection of:
    a) the respective active volume associated with the respective functional sub-sequence, and
    b) a subject volume comprising subject information that characterizes said examination subject.

5. A method as claimed in claim 4 comprising generating said subject information for said subject volume from image data generated by said magnetic resonance imaging system during operation of said magnetic resonance imaging system.

6. A method as claimed in claim 5 comprising generating said image data as an overview image, of at least a portion, of said examination subject.

7. A method as claimed in claim 1 comprising automatically determining at least a portion of said active volume position data from said supplied sequence control data.

8. A magnetic resonance imaging system comprising
a magnetic resonance data acquisition unit comprising a plurality of subsystems including a at least:
a gradient coil sub-system and
a shim sub-system; and
a control device that operates the subsystems in coordination with each other in order to implement a data acquisition sequence and in order to acquire magnetic resonance image data from an examination subject;
said control device having an input at which said control device receives sequence control data that defines a complete data acquisition sequence comprised of a plurality of respective different functional sub-sequences, each sub-sequence being associated with a respective active volume that is defined at a spatial location within the imaging system in which the respective functional sub-sequence is configured to be effective in said complete data acquisition sequence, the respective spatial locations of the active volumes for the respective sub-sequences being different from each other;
in addition to said sequence control data, said control device being configured to receive at said input, active volume position data respectively associated with each of the different functional sub-sequences, and in said active volume position data defining, for each of said active volumes, a position, orientation and extent of the respective active volume in the imaging system; and
said control device being configured to automatically generate respective control signals that operate each of the different subsystems in order to implement said complete data acquisition sequence, by using said sequence control data and said active volume position data, in order to locally optimize the respective different functional sub-sequences, at least with regard to a portion of the active volume associated with the respective functional sub-sequence, and to make said control signals available from an output of said control device in a form allowing the operation of said subsystems in order to implement said measurement sequence.

9. A non-transitory computer-readable storage medium encoded with programming instructions, said storage medium being loadable into a computerized control system of a magnetic resonance imaging apparatus that also comprises a plurality of subsystems including at least:
a gradient coil sub-system and
a shim sub-system that are controlled by said computerized control unit and which are coordinated with each other in order to implement a data acquisition sequence, said programming instructions causing said computerized control unit to:
receive sequence control data that defines a complete data acquisition sequence comprised of a plurality of respective different functional sub-sequences, each sub-sequence being associated with a respective active volume that is defined at a spatial location within the imaging system in which the respective functional sub-sequence is effective in said complete data acquisition sequence, the respective spatial locations of the active volumes for the respective different functional sub-sequences being different from each other;
in addition to said sequence control data, receive active volume position data respectively associated with each of the different functional sub-sequences, and in said active volume position data defining, for each of said active volumes, a position, orientation and extent of the respective active volume in the imaging system; and
automatically generate respective control signals that operate each of the different subsystems in order to implement said complete data acquisition sequence, by using said sequence control data and said active volume position data in order to locally optimize the respective different functional sub-sequences at least with regard to a portion of the active volume associated with the respective functional sub-sequence, and make said control signals available from an output of said control device in a form that operates said subsystems in order to implement said measurement sequence.

\* \* \* \* \*